United States Patent [19]
Rhee et al.

[11] Patent Number: 5,550,187
[45] Date of Patent: Aug. 27, 1996

[54] METHOD OF PREPARING CROSSLINKED BIOMATERIAL COMPOSITIONS FOR USE IN TISSUE AUGMENTATION

[75] Inventors: Woonza M. Rhee, Palo Alto; Richard A. Berg, Los Altos; Joel S. Rosenblatt, Palo Alto; Jacqueline A. Tefft, Redwood City; Larry J. Braga, Fremont; Thomas L. Smestad, Palo Alto, all of Calif.

[73] Assignee: Collagen Corporation, Palo Alto, Calif.

[21] Appl. No.: 287,549

[22] Filed: Aug. 8, 1994

Related U.S. Application Data

[63] Continuation-in-part of Ser. No. 236,769, May 2, 1994, which is a continuation-in-part of Ser. No. 198,128, Feb. 17, 1994, Pat. No. 5,413,791, which is a division of Ser. No. 922,541, Jul. 12, 1994, Pat. No. 5,328,955, which is a continuation-in-part of Ser. No. 433,441, Nov. 10, 1992, Pat. No. 5,162,430, which is a continuation-in-part of Ser. No. 274,071, Nov. 21, 1988, abandoned.

[51] Int. Cl.⁶ .............................. C08G 63/49; C08G 63/91
[52] U.S. Cl. .......................... 525/54.1; 523/113; 424/423
[58] Field of Search ........................... 525/54.1; 523/113; 424/423

[56] References Cited

U.S. PATENT DOCUMENTS

| | | | |
|---|---|---|---|
| 5,162,430 | 11/1992 | Rhee et al. | 525/54.1 |
| 5,292,802 | 3/1994 | Rhee et al. | 525/54.1 |
| 5,306,500 | 4/1994 | Rhee et al. | 424/422 |
| 5,328,955 | 7/1994 | Rhee et al. | 525/54.1 |

*Primary Examiner*—Nathan M. Nutter
*Attorney, Agent, or Firm*—Kathi Rafayko

[57] ABSTRACT

The present invention discloses a novel method for preparing crosslinked biomaterial compositions for use in the augmentation of soft or hard tissue. In general, the method comprises mixing a biocompatible polymer, which is preferably collagen, with a sterile, dry crosslinking agent, which is preferably a synthetic hydrophilic polymer such as a functionally activated polyethylene glycol. Also provided are preferred processes for preparing sterile, dry crosslinking agents contained within syringes for use in the method of the invention. Methods for sterilization of the crosslinking agent include, but are not limited to, sterile filtration, aseptic processing, and e-beam or gamma irradiation. Methods for providing augmentation of soft or hard tissue using crosslinked biomaterial compositions prepared according to the method of the invention are also disclosed.

14 Claims, 1 Drawing Sheet

FIG. 1

METHOD OF PREPARING CROSSLINKED BIOMATERIAL COMPOSITIONS FOR USE IN TISSUE AUGMENTATION

CROSS-REFERENCES

This application is a continuation-in-part of copending U.S. application Ser. No. 08/236,769, filed May 2, 1994, which is a continuation-in-part of U.S. application Ser. No. 08/198,128, filed Feb. 17, 1994, and now U.S. Pat. No. 5,413,791 which is a divisional of U.S. Application Ser. No. 07/922,541 filed Jul. 12, 1994 and now U.S. Pat. No. 5,328,955, issued Jul. 12, 1994, which is a continuation-in-part of U.S. application Ser. No. 07/433,441, filed Nov. 10, 1992 and now U.S. Pat. No. 5,162,430, issued Nov. 10, 1992, which is a continuation-in-part of U.S. application Ser. No. 07/274,071, filed Nov. 21, 1988, subsequently abandoned, which applications and issued patents are incorporated herein by reference in full, and to which currently pending applications we claim priority under 35 U.S.C. § 120.

FIELD OF THE INVENTION

In general, this invention relates to a method of preparing crosslinked biomaterial compositions, which preferably comprise collagen or other biocompatible polymer crosslinked using a synthetic hydrophilic polymer, for use in tissue augmentation and in the production of formed implants for various medical uses. The invention also provides an article of manufacture comprising a syringe containing a sterile, dry, crosslinking agent and processes for preparing sterile, dry crosslinking agents contained within syringes for use in the methods of the present invention.

BACKGROUND OF THE INVENTION

U.S. Pat. No. 5,162,430, issued Nov. 10, 1992 to Rhee et al., and commonly owned by the assignee of the present application, discloses collagen-synthetic polymer conjugates and methods of covalently binding collagen to synthetic hydrophilic polymers. Commonly owned U.S. Pat. No. 5,292,802, issued Mar. 8, 1994, discloses methods for making tubes comprising collagen-synthetic polymer conjugates. Commonly owned U.S. Pat. No. 5,306,500, issued Apr. 26, 1994, discloses methods of augmenting tissue with collagen-synthetic polymer conjugates.

Commonly owned U.S. Pat. No. 5,328,955, issued Jul. 12, 1994, discloses various activated forms of polyethylene glycol and various linkages which can be used to produce collagen-synthetic polymer conjugates having a range of physical and chemical properties. Commonly owned, copending U.S. application Ser. No. 08/306,242, filed Sep. 14, 1994, and now abandoned discloses methods for coating implants with collagen-synthetic polymer conjugates.

Commonly owned, allowed U.S. application Ser. No. 08/146,843, filed Nov. 3, 1993, discloses conjugates comprising various species of glycosaminoglycan covalently bound to synthetic hydrophilic polymers, which are optionally bound to collagen as well. Commonly owned, allowed U.S. application Ser. No. 08/147,227, filed Nov. 3, 1993, discloses collagen-polymer conjugates comprising chemically modified collagens such as, for example, succinylated collagen or methylated collagen, covalently bound to synthetic hydrophilic polymers to produce optically clear materials for use in ophthalmic or other medical applications.

Commonly owned U.S. application Ser. No. 08/236,769, filed May 2, 1994, discloses collagen-synthetic polymer matrices prepared using a multiple step reaction.

All publications cited above and herein are incorporated herein by reference to describe and disclose the subject matter for which it is cited.

In our earlier issued patents and applications described above, we disclosed biomaterial compositions comprising collagen or other biocompatible polymers crosslinked using synthetic hydrophilic polymers. These crosslinked compositions were generally prepared by mixing aqueous suspensions of collagen or biocompatible polymers with aqueous solutions of synthetic hydrophilic polymers. The resulting crosslinked biomaterial compositions could be used in a variety of medical applications, such as soft tissue augmentation and the preparation of biocompatible implantable devices.

Unfortunately, there was a major drawback to the method of preparing crosslinked biomaterial compositions described above: synthetic hydrophilic polymers, such as functionally activated polyethylene glycols, are highly reactive with water, as well as with collagen and other polymers having corresponding reactive groups such as, for example (and not by way of limitation), available amirto groups. The longer the synthetic hydrophilic polymer is exposed to water (or water-based carriers), the more of its activity is lost due to hydrolysis, resulting in partial to complete loss of crosslinking ability. Therefore, in order to avoid significant loss of crosslinking activity due to hydrolysis, the synthetic hydrophilic polymer must be thoroughly mixed with an aqueous carrier to prepare a homogeneous, aqueous crosslinker solution immediately prior to being mixed with an aqueous suspension of composition. Unfortunately, a certain amount of activity could still be expected to be lost, despite the speed of the operator preparing the composition.

While the above method for preparing crosslinked biomaterials compositions had its drawbacks with respect to preparing formed implants, it represented an even greater hurdle in the development of a viable commercial product for use in tissue augmentation. For example, the synthetic hydrophilic polymer could not be stored in an aqueous state because it would hydrolyze, nor could it be stored mixed with the collagen because the two components would react and form a non-extrudable gel within the syringe. Therefore, the synthetic hydrophilic polymer needed to be provided to a physician in dry form, then dissolved in an aqueous carrier immediately prior to mixing with the collagen suspension. The contemplated method required a number of preparatory steps that needed to be performed in rapid succession by the physician in order to provide successful tissue augmentation. In other words, the suggested process was cumbersome and certainly not "user friendly".

In the contemplated method, the physician would be provided with a syringe containing an appropriate amount of an aqueous carrier solution, such as phosphate-buffered saline (PBS), a vial containing an appropriate amount of a dry crosslinking agent, such as a synthetic hydrophilic polymer, and a relatively large-gauge needle, such as a 20-gauge needle. Prior to mixing the crosslinking agent with the collagen (which would be provided in its own syringe), the physician would need to perform the following steps: 1) unwrap the package containing the needle; 2) remove the cap from the syringe containing the aqueous carrier; 3) attach the needle to the syringe; 4) dispense the aqueous carrier by means of the needle into the vial containing the dry crosslinking agent; 5) vortex or otherwise adequately mix the crosslinking agent with the aqueous carrier within the vial to produce an aqueous crosslinker solution (which has already started to hydrolyze in the presence of water); 6) withdraw the crosslinker solution into the syringe; and 7) remove the needle from the syringe in preparation for mixing the crosslinker solution with the collagen (or other biomaterial). All of these preparatory steps would need to be performed within minutes of mixing the crosslinker solution with the collagen and injecting the patient in order to minimize loss of crosslinker activity.

SUMMARY OF THE INVENTION

In situ crosslinking of biocompatible polymers and crosslinking agents requires that the crosslinking agent and biocompatible polymer be uniformly mixed for formation of a strong, cohesive implant following injection. At the time the method described above was developed, it was not contemplated that it would be possible to obtain adequate mixing of crosslinking agents in dry form with a biocompatible polymer to achieve an evenly crosslinked implant. However, we have since discovered methods of mixing dry crosslinking agents with aqueous suspensions of collagen which result in the production of strong, evenly crosslinked implants. In fact, our experiments indicate that uniform mixing is achievable when aqueous suspensions of collagen are mixed with either dry crosslinking agents or with aqueous solutions of crosslinking agents. Uniform mixing results in crosslinked gels having good mechanical strength and low spatial variability in mechanical strength. Non-uniform mixing can lead to local regions of low crosslinker concentration within the gel, resulting in lower average gel strengths and greater variability in mechanical strength spatially across the gel.

Our experiments indicate that, surprisingly, crosslinked gels produced using dry crosslinking agents may have greater average strength, and less spatial variability in strength, than gels produced using aqueous solutions of crosslinking agents. We have attributed this unexpected result to the possibility that, because dry crosslinking agents must be solubilized prior to reacting with collagen, they may be expected to react more slowly with collagen than would aqueous crosslinking agents. Dry crosslinking agents must first be solubilized prior to reacting with collagen, allowing additional time before the initiation of gel network formation, during which time the crosslinking agent can be more homogeneously mixed with the collagen. The faster reaction times of aqueous crosslinking agents may lead to weaker gels because the crosslinked gel may fracture if mixing is still in progress while gel network formation is occurring.

An additional benefit exists for dry crosslinking agents which are hydrolytically unstable. When dry crosslinking agents are mixed with aqueous suspensions of collagen (or other biocompatible polymer), the reactive sites of the dry crosslinking agent are in contact with water for a shorter period of time before they can react with the collagen, which may result in greater crosslinking efficiency (crosslinking density) because the rate of aminolysis for crosslinking agents such as synthetic hydrophilic polymers is always faster than their rate of hydrolysis (e.g., for a synthetic hydrophilic polymer such as difunctionally activated SG-PEG, the rate of aminolysis is at least ten times greater than the rate of hydrolysis).

The optionization of techniques for mixing biocompatible polymers and dry crosslinking agents led to the development of a method for providing tissue augmentation having a reduced number of steps compared to the previously contemplated method. The present invention provides a method for preparing crosslinked biomaterial compositions comprising: providing a means for delivering a biocompatible polymer and a means for delivering a sterile, dry crosslinking agent; mixing the biocompatible polymer with the dry crosslinking agent to initiate crosslinking between the biocompatible polymer and the crosslinking agent; and delivering the biocompatible polymer and the crosslinking agent to a mold having the desired size and shape. The present invention also provides a method for effecting tissue augmentation that consists of a minimum number of steps and is therefore very "user friendly" to the physician. Said method comprises the steps of: providing a means for delivering a biocompatible polymer and a means for delivering a sterile, dry crosslinking agent; mixing the biocompatible polymer with the dry crosslinking agent to initiate crosslinking between the biocompatible polymer and the crosslinking agent; and delivering the biocompatible polymer and the crosslinking agent to the tissue site in need of augmentation.

Because the crosslinked biomaterial compositions prepared using the method of the invention are destined to be injected or otherwise implanted into a human body, it is necessary that the dry crosslinking agents be provided in a sterile form, and that they retain their sterility over long-term storage. We therefore developed several processes for preparing dry, sterile crosslinking agents contained within syringes.

One such process comprises dissolving a dry crosslinking agent in a fluid carrier to produce a crosslinker solution, sterile-filtering the crosslinker solution, dispensing the sterile crosslinker solution into a syringe, followed by lyophilizing the sterile crosslinker solution within the syringe under aseptic conditions. A similar process comprises dissolving a dry crosslinking agent in a fluid carrier to produce a crosslinker solution, dispensing the crosslinker solution into a syringe, lyophilizing the crosslinker solution within the syringe, then sterilizing the resulting dry crosslinking agent within the syringe using irradiation.

Yet another process involves dissolving a dry crosslinking agent in a nonaqueous carrier to produce a nonaqueous crosslinker solution, sterile-filtering the crosslinker solution, dispensing the sterile crosslinker solution into a syringe, and then drying the sterile crosslinking agent within the syringe by evaporation under aseptic conditions. A similar process comprises dissolving a dry crosslinking agent in a nonaqueous carrier to produce a nonaqueous crosslinker solution, dispensing the crosslinker solution into a syringe, drying the crosslinker solution within the syringe by evaporation, then sterilizing the dry crosslinking agent within the syringe by irradiation.

An alternative process comprises dispensing a dry crosslinking agent into a syringe, then sterilizing the dry crosslinking agent within the syringe using irradiation.

Sterile, dry crosslinking agents prepared as described above can be stored for long periods of time within a syringe (or other delivery means) while maintaining their activity (i.e., reactivity with biocompatible polymers) as well as their sterility.

We now disclose a detailed description of preferred embodiments of the present invention, including improved methods for preparing crosslinked biomaterial compositions and for effecting tissue augmentation using crosslinked biomaterial compositions, as well as methods for providing sterile, dry crosslinking agents contained within syringes.

DEFINITIONS

It must be noted that, as used in this specification and the appended claims, the singular forms "a", "an", and "the" include plural referents unless the context clearly dictates otherwise. For example, reference to "a conjugate" includes one or more conjugate molecules, reference to "an article" includes one or more different types of articles known to those skilled in the art and reference to "the collagen" includes mixtures of different types of collagens and so forth.

Specific terminology of particular importance to the description of the present invention is defined below:

The term "aqueous carrier" refers to a water-based fluid carrier, such as water-for-injection (WFI) or a solution of phosphate-buffered saline (PBS).

The term "atelopeptide collagen" refers to collagens which have been chemically treated or otherwise processed to remove the telopeptide regions, which are known to be responsible for causing an immune response in humans to collagens from other animal, such as bovine, sources.

The terms "chemically conjugated" and "conjugated" as used herein mean attached through a covalent chemical bond. In the practice of the invention, a hydrophilic synthetic polymer and a biocompatible polymer molecule may be covalently conjugated directly to each other by means of a functional group on the synthetic hydrophilic polymer, or the biocompatible polymer and the synthetic polymer may be covalently conjugated using a linking radical, so that the hydrophilic synthetic polymer and the biocompatible polymer are each bound to the radical, but not directly to each other.

The term "collagen" as used herein refers to all types and forms of collagen, including those which have been recombinantly produced, extracted from naturally occurring sources (such as bovine corium or human placenta), processed, or otherwise modified.

The term "collagen-in-solution" or "CIS" refers to collagen in an acidic solution having a pH of approximately 3 or less, such that the collagen is in the nonfibrillar form.

The term "collagen suspension" refers to a suspension of collagen fibers in an aqueous carrier, such as water or phosphate-buffered saline (PBS).

The term "collagen-synthetic polymer" refers to collagen chemically conjugated to a synthetic hydrophilic polymer, within the meaning of this invention. For example, "PEG-collagen" denotes a composition of the invention wherein molecules of collagen are covalently conjugated to molecules of polyethylene glycol (PEG).

"Crosslinked collagen" refers to a collagen composition in which collagen molecules are linked by covalent bonds with multifunctionally activated synthetic hydrophilic polymers, such as difunctionally activated polyethylene glycol.

The term "difunctionally activated" refers to synthetic hydrophilic polymer molecules which have been chemically derivatized so as to have two functional groups capable of reacting with primary amino groups on biocompatible polymer molecules, such as collagen or deacetylated glycosaminoglycans. The two functional groups on a difunctionally activated synthetic hydrophilic polymer are generally located at opposite ends of the polymer chain. Each functionally activated group on a difunctionally activated synthetic hydrophilic polymer molecule is capable of covalently binding with a biocompatible polymer molecule, thereby effecting crosslinking between the biocompatible polymer molecules.

The term "dry" means that substantially all unbound water has been removed from a material.

The term "fibrillar collagen" refers to collagens in which the triple helical molecules aggregate to form thick fibers due to intermolecular charge and hydrophobic interactions.

The term "fluid carrier" refers to a flowable carrier which may be either an aqueous or a nonaqueous carrier, as specified.

The term "functionally activated" refers to synthetic hydrophilic polymers which have been chemically derivatized so as to have one or more functional group capable of reacting with primary amino groups on biocompatible polymer molecules.

The term "in situ" as used herein means at the site of administration.

The term "in situ crosslinking" as used heroin refers to crosslinking of a biocompatible polymer implant following implantation to a tissue site on a human or animal subject, wherein at least one functional group on the synthetic polymer is covalently conjugated to a biocompatible polymer molecule in the implant, and at least one functional group on the synthetic polymer is free to covalently bind with other biocompatible polymer molecules within the implant, or with collagen molecules within the patient's own tissue.

The term "lyophilized" refers to a dry state which has been achieved by freezing a wet substance and evaporating the resulting ice. Lyophilization is intended to preserve wet substances. The product is frozen, then exposed to an atmosphere of low relative humidity in which the ice contained within the product sublimes, i.e., transforms directly from a solid to a vapor without melting. The necessary low relative humidity is generally achieved by conducting the process under a vacuum.

The term "molecular weight" as used herein refers to the weight average molecular weight of a number of molecules in any given sample, as commonly used in the art. Thus, a sample of PEG 2000 might contain a statistical mixture of polymer molecules ranging in weight from, for example, 1500 to 2500, with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20,000.

The term "multifunctionally activated" refers to synthetic hydrophilic polymers which have been chemically derivatized so as to have two or more functional groups which are located at various sites along the polymer chain and are capable of reacting with primary amino groups on biocompatible polymer molecules. Each functional group on a multifunctionally activated synthetic hydrophilic polymer molecule is capable of covalently binding with a biocompatible polymer molecule, thereby effecting crosslinking between the biocompatible polymer molecules. Types of multifunctionally activated hydrophilic synthetic polymers include difunctionally activated, tetrafunctionally activated, and star-branched polymers.

The term "nonaqueous carrier" refers to a fluid carrier which is not water-based, such as acetone or an alcohol such as ethanol.

The term "nonfibrillar collagen" refers to collagens in which the triple helical molecules do not aggregate to form thick fibers, such that a composition containing nonfibrillar collagen will be optically clear.

The term "sterile filtration" refers to removal of microbial contaminants from a solution by passing the solution through a filter having pores of a diameter small enough that microbial contaminants will not pass through the filter pores with the solution that is being decontaminated.

The terms "synthetic hydrophilic polymer" or "synthetic polymer" refer to polymers which have been synthetically produced and which are hydrophilic, but not necessarily water-soluble. Examples of synthetic hydrophilic polymers which can be used in the practice of the present invention are polyethylene glycol (PEG), polyoxyethylene, polymethylene glycol, polytrimethylene glycols, polyvinylpyrrolidones, polyoxyethylene-polyoxypropylene block polymers and copolymers, and derivatives thereof. Naturally occurring polymers such as proteins, starch, cellulose, heparin, hyaluronic acid, and derivatives thereof are expressly excluded from the scope of this definition.

The term "syringe" refers to a device which is adapted for the injection of a material to a tissue site, which may be soft or hard tissue.

The term "tissue augmentation" as used herein refers to the replacement or repair of defects in the soft or hard tissues of a human body.

Except as otherwise defined above, all technical and scientific terms used herein have the same meaning as commonly understood by one of ordinary skill in the art to which this invention belongs. Although any methods and materials similar or equivalent to those described herein may be useful in the practice or testing of the present invention, only the preferred methods and materials are described below. It is not intended that the invention be limited to these preferred embodiments, however. The invention is intended to have the scope defined by the attached claims.

DETAILED DESCRIPTION OF THE PREFERRED EMBODIMENTS OF THE INVENTION

In order to practice the methods of the present invention, it is first necessary to provide a biocompatible polymer, such as, for example, collagen or a glycosaminoglycan, and a sterile, dry crosslinking agent, such as a synthetic hydrophilic polymer or a carbodiimide.

Collagen, or derivatives thereof, may be used as the biocompatible polymer in the methods of the present invention. Lysine residues on collagen molecules contain primary amino groups capable of reacting with synthetic hydrophilic polymers; therefore, collagen can be used in its natural, purified state and need not be chemically modified in order to form covalently bound conjugates with synthetic hydrophilic polymers.

Collagen from any source may be used in the practice of the invention; for example, collagen may be extracted and purified from human or other mammalian source, or may be recombinantly or otherwise produced. Collagen of any type may be used, including, but not limited to, types I, II, III, IV, or any combination thereof, although type I is generally preferred. Atelopeptide collagen is generally preferred over telopeptide-containing collagen because of its reduced immunogenicity. Collagens that have been previously crosslinked by radiation, heat, or other chemical crosslinking agents such as glutaraldehyde may be used, but are generally not preferred. The collagen should be in a pharmaceutically pure form such that it can be incorporated into a human body without generating any significant immune response.

Nonfibrillar collagens, including those that have been chemically modified, such as succinylated collagen or methylated collagen, may be used in the practice of the invention, but they are not generally preferred. Fibrillar collagens are generally preferred for use in soft tissue augmentation because their ability to form thick, robust fibers has been demonstrated to result in greater persistence in vivo than nonfibrillar collagens. Fibrillar collagen prepared by methods known in the art or commercially available atelopeptide fibrillar collagen compositions, such as Zyderm® I Collagen (35 mg/ml collagen concentration) or Zyderm II Collagen (65 mg/ml collagen concentration), are preferred collagens for use in the methods of the present invention. The collagen concentration of a collagen suspension should generally be within the range of about 10 mg/nal to about 120 mg/ml, most preferably, in the range of about 30 mg/ml to about 70 mg/ml. The collagen concentration of commercially available collagen compositions can be decreased by fixing the collagen composition with an appropriate amount of sterile water or phosphate buffered saline (PBS). Conversely, to increase the collagen concentration, the collagen composition can be concentrated by centrifugation, then adjusted to the desired collagen concentration by mixing with an appropriate amount of sterile water or PBS.

Glycosaminoglycans, such as, for example, hyaluronic acid, chondroitin sulfate A, chondroitin sulfate C, dermatan sulfate, keratan sulfate, keratosulfate, chitin, chitosan, heparin, and derivatives or mixtures thereof, may be used as the biocompatible polymer in the methods of the present invention. Different types of glycosaminoglycans can be mixed together, or mixed with collagen, and used in the practice of the invention. Glycosaminoglycans must generally be modified, such as by deacetylation or desulfation, in order to provide primary amino groups capable of binding with functional groups on synthetic hydrophilic polymers. Methods for chemically modifying glycosan-tinoglycans in such a manner that they are capable of binding with synthetic hydrophilic polymers are described in commonly owned, copending U.S. application Ser. No. 08/146,843, filed Nov. 3, 1993. In general, glycosaminoglycans can be deacetylated, desolated, or both, as applicable, by the addition of a strong base, such as sodium hydroxide, to the glycosaminoglycan. The deacetyled and/or desulfated glycosaminoglycan is capable of covalently binding with a functionally activated synthetic hydrophilic polymer.

Any biocompatible crosslinking agent that is available in dry form, or can be processed to be in dry form while still retaining crosslinking activity, can be used in the device and method of the present invention. However, synthetic hydrophilic polymers, such as functionally activated polyethylene glycols, are the preferred crosslinking agents, with difunctionally activated polyethylene glycols being most preferred. Various activated forms of polyethylene glycol are described below.

Specific Forms of Activated Polyethylene Glycol

For use in the present invention, molecules of polyethylene glycol are chemically modified in order to provide functional groups on one or, preferably, two or more sites along the length of the PEG molecule, so that covalent binding can occur between the PEG and the reactive groups on the biocompatible polymer. Some specific activated forms of PEG are shown structurally below, as are generalized reaction products obtained by reacting activated forms of PEG with collagen. In Formulas 1–7, the term COL represents collagen. The term PEG represents polymers having the repeating structure $(OCH_2CH_2)_n$.

The first activated PEG is difunctionally activated PEG succinimidyl glutarate, referred to herein as (SG-PEG). The structural formula of this molecule and the reaction product obtained by reacting it with collagen are shown in Formula 1.

SG-PEG: Difunctionally Activated PEG Succinimidyl Glutarate

Another difunctionally activated form of PEG is referred to as PEG succinimidyl (S-PEG). The structural formula for this compound and the reaction product obtained by reacting it with collagen is shown in Formula 2. In any general structural formula for the compound, the subscript 3 is replaced with an "n". In the embodiment shown in Formula 1, n=3, in that there are three repeating $CH_2$ groups on either side of the PEG. The structure in Formula 2 results in a conjugate which includes an "ether" linkage which is not subject to hydrolysis. This is distinct from the conjugate shown in Formula 1, wherein an ester linkage is provided. The ester linkage is subject to hydrolysis under physiological conditions.

S-PEG, n=3: Difunctionally Activated PEG Succinimidyl

FORMULA 2

Yet another difunctionally activated form of polyethylene glycol, wherein n=2, is shown in Formula 3, as is the conjugate formed by reacting the activated PEG with collagen.

S-PEG, n=2: Difunctionally Activated PEG Succinimidyl

FORMULA 1

Another preferred embodiment of the invention similar to the compounds of Formulas 2 and 3 is provided when n=1. The structural formula and resulting collagen-synthetic polymer conjugate are shown in Formula 4. It is noted that this conjugate includes both an ether and a peptide linkage. These linkages are stable under physiological conditions.

S-PEG, n=1: Difunctionally Activated PEG Succinimidyl

FORMULA 4

Yet another difunctionally activated form of PEG is provided when n=0. This compound is referred to as PEG succinimidyl carbonate (SC-PEG). The structural formula of this compound and the conjugate formed by reacting SC-PEG with collagen is shown in Formula 5.

SC-PEG, n=0: Difunctionally Activated PEG Succinimidyl Carbonate

All of the activated polyethylene glycol derivatives depicted in Formulas 1–5 involve the inclusion of the succinimidyl group. However, different activating groups can be attached at sites along the length of the PEG molecule. For example. PEG can be derivatized to form difunctionally activated PEG propion aldehyde (A-PEG), which is shown in Formula 6, as is the conjugate formed by the reaction of A-PEG with collagen. The linkage shown in Formula 6 is referred to as a $-(CH_2)_n-NH-$ linkage, where n=1–10.

A-PEG: Difunctionally Activated PEG Propion Aldehyde

Yet another form of activated polyethylene glycol is difunctionally activated PEG glycidyl ether (E-PEG), which is shown in Formula 7, as is the conjugate formed by reacting such with collagen.

E-PEG: Difunctionally Activated PEG Glycidyl Ether

Many of the activated forms of polyethylene glycol described above are now available commercially from Shearwater Polymers, Huntsville, Ala., and Union Carbide, South Charleston, W.V. The various activated forms of polyethylene glycol and various linkages which can be used to produce collagen-syntactic polymer conjugates having a range of physical and chemical properties are described in further detail in commonly owned U.S. Pat. No. 5,328,955, issued Jul. 12, 1994.

The concentration of crosslinking agent used in the practice of the invention will vary depending on the type and concentration of biocompatible polymer used, the type of crosslinking agent used, the molecular weight of the crosslinking agent, and the degree of crosslinking desired.

For example, when reacting a suspension of collagen (which has a molecular weight of approximately 300,000) having a collagen concentration of approximately 35 mg/ml with a difunctionally activated SG-PEG having a molecular weight of approximately 3800, the concentration of SG-PEG used is generally within the range of about 1 milligram to about 20 milligrams of difunctionally activated SG-PEG (DSG-PEG) per milliliter of collagen suspension, representing a molar ratio of between about 2 to about 48 moles of DSG-PEG per mole of collagen. When using a suspension of collagen having a collagen concentration of approximately 65 mg/ml, the concentration of difunctionally activated SG-PEG used is generally within the range of about 2 milligrams to about 40 milligrams of SG-PEG per milliliter of collagen suspension.

Preparation of a Sterile, Dry Crosslinking Agent Contained Within a Syringe

Various methods can be used to prepare sterile, dry crosslinking agents contained within syringes for use in the methods of the present invention. Preferred methods are described below.

In Method A, a dry crosslinking agent is dissolved in a fluid carrier, which may be an aqueous carrier or a nonaqueous carrier. Suitable nonaqueous carriers include ethanol, methylene chloride, acetone, or chloroform, with ethanol being particularly preferred. If an aqueous carrier is used in conjunction with a water-reactive crosslinking agent, such as a functionally activated polyethylene glycol, the carrier should be maintained at a slightly acidic pH, preferably, between about pH 3 and about pH 5, in order to retard hydrolysis of the crosslinking agent. After the crosslinking agent has been dissolved in the fluid carrier, the resulting crosslinker solution is sterile-filtered through one or more filters having pore sizes of 0.22 microns or smaller to produce a sterile crosslinker solution. The sterile crosslinker solution is then dispensed into syringes (preferably, about 3 cc in volume), each of which is then fitted with a sterile barrier cap, such as a 0.2 micron hydrophobic polytetrafluoroethylene (PTFE) membrane. The sterile crosslinker is then lyophilized aseptically within the syringe to produce a sterile, dry crosslinking agent.

In a method similar to Method A, above, a dry crosslinking agent is dissolved in a fluid carrier, which may be an aqueous carrier or a nonaqueous carrier. After the crosslinking agent has been dissolved in the fluid carrier, the resulting crosslinker solution is then dispensed into syringes, each of which is fitted with a sterile barrier cap, and lyophilized within the syringe to produce a dry crosslinking agent. The dry crosslinking agent is then sterilized inside the syringe using irradiation, which is preferably e-beam or gamma irradiation.

In an alterative method, Method B, a dry crosslinking agent is dissolved in a nonaqueous carrier. The resulting nonaqueous crosslinker solution is then sterile-filtered through one or more filters having pore sizes of 0.22 microns to produce a sterile crosslinker solution. The sterile crosslinker solution is then dispensed into syringes and dried inside the syringes by evaporation under vacuum at a temperature in the range of about 10° C. to about 20 C. under aseptic conditions. When a nonaqueous carrier is used with a water-reactive crosslinking agent, there is no need to worry about loss of crosslinking activity due to hydrolysis.

In a method similar to Method B, above, a dry crosslinking agent is dissolved in a nonaqueous carrier. The resulting nonaqueous crosslinker solution is then dispensed into syringes and dried by evaporation under vacuum at a temperature in the range of about 10° C. to about 20° C. The dry crosslinking agent is then sterilized inside the syringes using irradiation, which is preferably e-beam or gamma irradiation.

In yet another method, Method C, a dry crosslinking agent is first dispensed into syringes, then sterilized inside the syringes using irradiation, preferably e-beam or gamma irradiation. Irradiation of the dry crosslinking agent within the syringe is preferably performed in the absence of oxygen to minimize oxidation of the crosslinking agent during the irradiation process.

To facilitate dispensing of the crosslinking agent into syringes, the dry crosslinking agent may be compressed into a mold to form a pellet and/or mixed (prior to molding) with a filler material such as a biocompatible dry inert agent in order to increase the volume of crosslinking agent to be dispensed into each syringe. Suitable dry inert agents include unactivated polyethylene glycols, sugars, salts, or carbohydrates. Preferred inert agents include glucose and sodium chloride. Dry inert agents are generally added to the dry crosslinking agent in a ratio of between about 5 to about 50 milligrams of dry inert agent per milligram of crosslinking agent and, preferably, between about 20 to about 30 milligrams of inert agent per milligram of crosslinking agent.

Method of Preparing Crosslinked Biomaterial Compositions

In order to practice the method of the present invention, it is first necessary to provide a means for delivering a biocompatible polymer, such as collagen or a glycosaminoglycan derivative, and a means for delivering a sterile, dry crosslinking agent, such as a synthetic hydrophilic polymer. Syringes are the presently preferred means for delivering the biocompatible polymer and the crosslinking agent, although other devices, such as compressed air injectors, may be utilized. We have discovered that optimum crosslinking is achieved when the syringe containing the biomaterial or the syringe containing the dry crosslinking agent (or both syringes) has a contraction ratio (i.e., the ratio of the inner diameter of the barrel to the inner diameter of the syringe exit orifice) of about 4.0 or greater. Preferred syringes for use in the present invention have a barrel volume of about 3 cc, a barrel diameter of about 8.5 mm, an exit orifice diameter of about 2 mm, and a contraction ratio of about 4.25. To achieve optimum mixing, the preferred volume of biomaterial contained within the syringe is between about 1 cc and about 2 cc. Non-uniform mixing could lead to the creation of regions of low crosslink density within an implant, which could significantly weaken it, leading to poor persistence. Poor mixing could also create regions of high local crosslinker concentration within the implant; the excess crosslinker could leach into tissues surrounding the implant, rather than serving to crosslink the implant or to anchor the implant to adjacent tissue.

In a preferred method for preparing crosslinked biomaterial compositions, a syringe containing a biomaterial and a syringe containing a sterile, dry crosslinking agent are provided. The syringe containing the biomaterial and the syringe containing the dry crosslinking agent are then connected by means of syringe connector. Once the connection between the two syringes has been established, the biomaterial and the dry crosslinking agent are mixed back and forth between the syringe. When the biomaterial and crosslinking agent have been adequately mixed, all of the material is transferred into one of the two original syringes, or into a third syringe. The material can then be extruded from the syringe orifice into molds of the desired size and shape to produce a variety of formed implants, including tubular implants for use as vascular grafts or stents, or it can be extruded onto one or more surface of a preformed synthetic implant, such as a bone prosthesis or synthetic vascular graft or stent, to provide a crosslinked, nonimmunogenic biomaterial coating on the surface of the implant. Alternatively, a needle can be attached to the syringe from which the material can be extruded to provide soft tissue augmentation in a patient.

The material must be extruded from the syringe before complete crosslinking has occurred between the biocompatible polymer and the crosinking agent. The amount of time required for complete crosslinking to be achieved depends on a variety of factors, including the type and concentration of biocompatible polymer used, the type and concentration of crosslinking agent used, and the temperature and pH of the materials. For example, when a collagen suspension having a collagen concentration of approximately 35 mg/ml and a pH of approximately 7 is reacted with a difunctionally activated SG-PEG (DSG-PEG, 3800 MW) at a concentration of about 1–20 milligrams DSG-PEG per milliliter of collagen suspension, complete crosslinking between the collagen and the DSG-PEG at room temperature is generally achieved within 20 to 30 minutes of the initiation of mixing between the two components. The crosslinking reaction will generally proceed more slowly if the reaction is performed at a lower temperature and/or lower pH.

In a preferred method for providing soft tissue augmentation, a physician is provided with a kit comprising the following: one 3-cc syringe containing a biocompatible polymer, which is preferably collagen; one 3-cc syringe containing a sterile, dry crosslinking agent, which is preferably a synthetic hydrophilic polymer such as a functionally activated polyethylene glycol; one empty 1-cc syringe; one syringe connector (such as a three-way stopcock); and one or more needles, which are preferably 25-gauge or smaller, more preferably, 27-gauge or smaller and, most preferably, 30-gauge. The size of the needles provided will depend on the intended site of application of the crosslinked biomaterial. For example, for hard tissue applications or soft tissue applications such as sphincter augmentation, a 25-gauge or smaller needle is acceptable. However, for soft tissue applications such as dermal contour correction in the face, a 27-gauge or smaller needle is required, with a 30-gauge needle being most preferred.

The physician connects the syringe containing the biomaterial with the syringe containing the dry crosslinking agent by means of the syringe connector. He/she then mixes the biomaterial and crosslinking agent back and forth between the syringes, preferably employing at least 20, and, preferably, at least 30, passes of material between the syringes (one pass is counted each time the volume of material passes through the syringe connector). When the biomaterial and crosslinking agent have been adequately mixed, the physician transfers all of the material into one of the 3-cc syringes, detaches the empty 3-cc syringe from the syringe connector, attaches the empty 1-cc syringe to the 3-cc syringe containing biomaterial and crosslinking agent by means of the syringe connector, then transfers the entire contents of the 3-cc syringe into the formerly empty 1-cc syringe. He/she then attaches one of the needles to the full 1-cc syringe and injects the biomaterial and crosslinking agent, which have since initiated crosslinking, to the tissue site in need of augmentation. Preferably, treatment of the patient is completed within 20 to 30 minutes of mixing the biomaterial and the crosslinking agent.

In a less preferred embodiment, the biocompatible polymer and the sterile, dry crosslinking agent are contained in separate barrels of a double-barreled syringe which has a chamber or compartment housing a means for mixing the polymer and, the crosslinking agent in advance of the syringe orifice. When the physician exerts pressure on the syringe plunger, the biocompatible polymer and dry crosslinking agent are both extruded into the mixing chamber, where mixing and some preliminary crosslinking of the biocompatible polymer with the crosslinking agent occur prior to their extrusion from the needle to the intended tissue site, where further crosslinking takes place.

In another, less preferred embodiment, a lyophilized biocompatible polymer, a sterile, dry crosslinking agent, and a biocompatible fluid carrier are all contained in the barrel of one syringe, with the three components being separated one from the other by means of sterile barriers. When depressed by the physician, the syringe plunger pierces the sterile barriers, allowing the three components—biocompatible polymer, crosslinking agent, and fluid carrier—to come in contact with one another, rehydrate, and mix prior to being delivered from the syringe needle to the tissue site in need of augmentation.

EXAMPLES

The following examples are put forth so as to provide those of ordinary skill in the art with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1

(Mixing Efficiency of Dry and Aqueous Crosslinkers With Collagen Suspensions)

The following experiment was performed to evaluate the mixing efficiency of difunctionally activated SG-PEG (DSG-PEG, 3800 MW) and collagen under several different mixing protocols, as set forth in Table 1. Variables examined, included syringe size, number of mixing passes, and whether the DSG-PEG was in aqueous solution (liquid) or dry (powder) form.

TABLE 1

Mixing Protocols for Collagen/DSG-PEG Formulations

| DSG-PEG Syringe Size (cc) | Collagen Syringe Size (cc) | Form of DSG-PEG | # of Mixing Passes | Sample Code |
|---|---|---|---|---|
| 1 | 1 | Liquid | 20 | 1:1L20 |
| 1 | 1 | Liquid | 40 | 1:1L40 |
| 1 | 3 | Liquid | 20 | 1:3L20 |
| 1 | 3 | Powder | 20 | 1:3P20 |
| 1 | 3 | Liquid | 40 | 1:3L40 |
| 1 | 3 | Powder | 40 | 1:3P40 |
| 3 | 3 | Liquid | 20 | 3:3L20 |
| 3 | 3 | Powder | 20 | 3:3P20 |
| 3 | 3 | Liquid | 40 | 3:3L40 |
| 3 | 3 | Powder | 40 | 3:3P40 |

Syringes having a barrel volume of 1-cc (Part No. 4174, CIMCO Medical Corporation, Costa Mesa, Calif.) had an inner barrel diameter of 5.5 mm, a barrel length of 70 mm, and an orifice inner diameter of 2.5 min. Syringes having a barrel volume of 3-cc (Part No. 309585, Becton Dickinson Corporation, Franklin Lakes, N.J.) had an inner barrel diameter of 8.5 mm, a barrel length of 60 mm orifice inner diameter of 1.8 mm.

Samples involving aqueous solutions of DSG-PEG were prepared according to the following procedure: 0.9 gram of Zyderm® I Collagen was weighed into a 1-cc syringe (samples 1:1L20 and 1:ILA40) or into a 3-cc syringe (samples 1:3L20, 1:3L40, 3:3L20, and 33L40). Ten (10) milligrams of dry DSG-PEG was weighed into a rarer Eppendorf tube. Two hundred (200) microliters of 0.02M phosphate-buffered saline (PBS, pH=7.3) was then pipetted into the tube. The sample was vonexed for 1 minute, then 100 milliliters of the sample was pipetted into the barrel of a 1-cc syringe (samples 1:1L20, 1:1L40, 1:3L20, 3L40) or a 3-cc syringe (samples 3:3L20 and 3:3L40). The DSG-PEG solution was compressed to the tip of the syringe using the syringe plunger. Care was taken to expel all trapped air, yet retain all of the crosslinker solution. The collagen in its syringe was also compressed to the tip, so as to expel all trapped air, yet retain all of the collagen.

Samples involving dry DSG-PEG were prepared according to the following procedure: One (1.0) gram of Zyderm® I Collagen was weighed into a 3-cc syringe. Five (5) milligrams of DSG-PEG powder was weighed into either a 1-cc syringe (samples 1:3P20 and 1:3P40) or a 3-cc syringe (samples 3:3P20 and 3:3P40). The DSG-PEG powder was compressed to the tip of the syringe using its plunger. Care was taken to expel all air from the syringe, yet retain all of the SG-PEG powder. The collagen in its syringe was compressed to the tip so as to expel all trapped air, yet retain all of the collagen.

All samples were mixed according to the following procedure: A three-way stopcock (Catalog No. K75, Baxter Healthcare Corporation, PhamaSeal Division, Valencia, Calif.) was connected to the syringe containing the collagen. The collagen was extruded through the connector orifice so that there would be no trapped air when the syringe containing the DSG-PEG was connected, but also so that no collagen was lost. The syringe containing the DSG-PEG (in solution or dry) was connected to the stopcock - collagen syringe assembly. Mixing of the DSG-PEG and the collagen was performed by simple exchange between syringes. One pass was counted each time the volume of the DSG-PEG-collagen mixture passed through the stopcock. Plunger strokes were made as quickly as possible. In general, all of the mixing (from first pass to last) was accomplished within 1 minute. After mixing was completed and the entire volume of mixture was contained in one syringe, the empty mixing syringe was removed and replaced with a clean 1-cc syringe. The DSG-PEG - collagen mixture was loaded by compression into the clean 1-cc syringe, which was then capped and placed in a 37° C. incubator to crosslink overnight, forming a gel.

The tip end of the 1-cc syringe was cut off and the plunger used to gently eject the cylindrical gel from the syringe. The gel was subsequently sectioned into 4-mm thick disks for mechanical strength testing. Samples were compressed to failure in the Instron Universal Tester, Model 4202, at a constant rate of 2 millimeters per minute. Results of compression testing are presented in Table 2. Sample position is listed starting from the tip to the plunger end of the syringe. Samples that had air bubbles or that were too thick are not included in the results.

TABLE 2

Compression Testing of Collagen - DSG-PEG Gels

Force to Failure (in Newtons)
Sample Code

| Sample Position | 1:1 L20 | 1:1 L40 | 1:3 L20 | 1:3 P20 | 1:3 L40 | 1:3 P40 | 3:3 L20 | 3:3 P20 | 3:3 L40 | 3:3 P40 |
|---|---|---|---|---|---|---|---|---|---|---|
| Tip | 7.6 | 5.5 | 13.9 | 12.3 | 9.8 | 8.3 | 13.5 | 8.5 | 11.6 | 12.5 |
| Tip + 1 | 5.6 | 7.8 | 16.1 | 8.3 | 7.9 | 8.0 | 14.6 | 12.4 | 9.3 | 14.5 |
| Tip + 2 | n/a | 10.5 | 12.1 | 8.4 | 11.1 | 8.2 | 10.3 | 10.7 | 11.6 | 10.8 |
| Tip + 3 | 6.1 | 11.6 | 9.2 | 9.2 | 9.1 | 8.0 | 11.4 | 10.8 | 10.9 | 10.8 |
| Tip + 4 | 9.0 | 9.8 | 5.0 | n/a | 9.8 | 9.2 | 12.3 | 11.9 | n/a | 9.0 |
| Tip + 5 | 7.1 | 10.3 | 8.6 | 9.8 | 9.1 | 10.4 | n/a | n/a | 8.4 | n/a |
| Tip + 6 | n/a | 10.8 | 8.7 | 7.9 | 8.4 | 10.4 | n/a | n/a | 7.7 | n/a |
| Tip + 7 | n/a | n/a | 5.5 | n/a | n/a | 9.2 | n/a | n/a | n/a | n/a |
| Plunger | 11.4 | 10.1 | 3.3 | 9.7 | 10.6 | 8.2 | 12.5 | n/a | 11.7 | n/a |
| N = | 6 | 8 | 9 | 7 | 8 | 9 | 6 | 5 | 7 | 5 |
| Mean | 7.8 | 9.6 | 9.2 | 9.4 | 9.5 | 8.9 | 12.4 | 10.9 | 10.2 | 11.5 |
| Range* | 5.8 | 6.1 | 12.8 | 4.4 | 3.2 | 2.4 | 4.3 | 3.9 | 3.3 | 5.5 |

Range = highest value minus lowest value.

Failure force measurements are heavily influenced by the presence of physical defects in the gel samples. The purpose of applying this type of measurement was to detect defects resulting from poor mixing of collagen and crosslinker. Mixing defects consist of regions of low crosslinker concentration, as well as the creation of stress planes by deforming the gel as network formation was occurring, essentially acting to fragment the gel. It is important to form strong, uniformly crosslinked gels because, when implanted in vivo, weaker gels tend to be displaced and deformed more over time by pressures exerted by the surrounding tissue than would strong gels.

Figure 1:
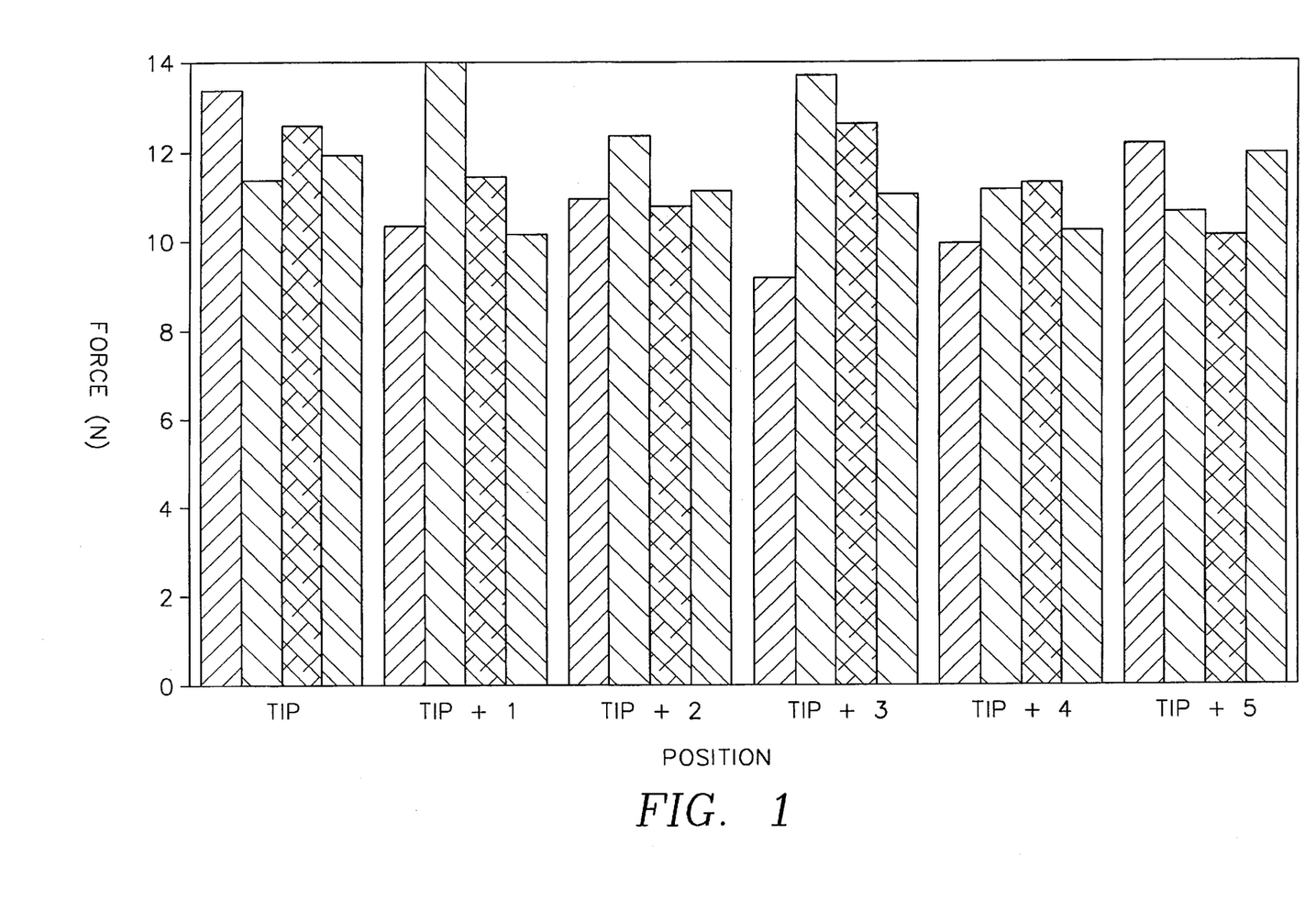
FIG. 1 shows the results of mechanical compression testing for crosslinked collagen-gels having a 35 mg/ml collagen concentration and a 5 mg/ml concentration of difunctionally activated SG-PEG (DSG-PEG) powder, which were prepared by mixing the collagen and dry DSG-PEG back and forth between two syringes, each having a barrel volume of 3 cc, for a total of 40 passes between the two syringes (3:3P40). The gels were allowed to cure for 6 hours at 37°C., then sectioned into 4-mm thick disks for mechanical testing. Samples were compressed to failure in the Insiron Universal Tester, Model 4202, at a constant rate of 2 millimeters per minute. Force (in Newtons) required to cause failure of the gel is graphed against position of the sample from the syringe tip.

Variability in gel strength measurements was examined by preparing four gels identical to sample 3:3P40. The gels were allowed to cure for 6 hours at 37° C. and then were sectioned into 4-mm thick disks for mechanical testing. Results of mechanical compression testing are presented in FIG. 1. The results show that, with the exception of one measurement, all samples possessed failure strengths greater than 10 Newtons, with a scatter about the mean of up to 2 Newtons (i.e., a range of about 4 Newtons). There is insignificant variability in gel strength from the tip of the syringe to the plunger end. This material may therefore be concluded to have good mixing.

Based on the results of our experiments, two interpretation guidelines can be drawn: 1) disks with gel strengths of approximately 6 Newtons or less (representing more than two times the scatter that could be expected from preparation variability) can be considered weak; weak gels are indicative of areas of low local crosslinker concentration resulting from poor mixing; 2) trends in disk strength or variations in disk strength beyond the expected 2 Newton scatter suggest poor mixing of the collagen and crosslinker.

Based on the above interpretation guidelines, the gels prepared by mixing between 1-cc syringes displayed trends (sample 1:1L40) or variability (1:1L20) strongly suggestive of poor mixing. There are several sections within these two gels (especially for sample 1:1L20) that are very weak. Gels mixed for 40 passes showed significant improvement in mechanical properties as compared to the gels mixed for only 20 passes.

Mixing between 1- and 3-cc syringes using DSG-PEG in aqueous solution shows a similar improvement as the number of passes are increased. The gels mixed for 20 passes clearly show a trend in strength according to gel position and there are weak sections in the gel, indicating insufficient mixing. Forty passes appears to give reasonable mixing and uniform strength in a range indicative of reasonable crosslink densities.

Mixing between 1- and 3-cc syringes using DSG-PEG powder appears to give adequate mixing. However, the strengths of several of the disks are on the low end (approximately 8 Newtons) of the expected variability range.

Mixing between 3-cc syringes, with either aqueous or powder forms of DSG-PEG, gave uniformly strong gel sections within the variability range. There appears to be one weak spot in sample 3:3L40; given the average higher strength of 3:3L20, which had less mixing time, this is likely a result of stress plane generation resulting from continued mixing of the sample after gel formation had been initiated.

Example 2

(Preparation of a Sterile, Dry Crosslinking Agent: Lyophilization of Difunctionally Activated SG-PEG)

Fifteen hundred (1500) milligrams of difunctionally activated SG-PEG (DSG-PEG, 3800MW) was mixed with 150 milliliters of water-for-injection (WFI, pH 4.5), resulting in a final DSG-PEG concentration of approximately 10 mg/ml. The DSG-PEG solution was then sterile-filtered through a Durapore filter having a pore size of 0.22 microns (Millipore Corporation, Bedford, Mass.). 0.5 milliliter of DSG-PEG solution was aliquotted into each of 180 3-cc syringes. Each syringe was then fitted with a sterile barrier cap comprising a 0.2 micron hydrophobic polytetrafluoroethylene membrane (Part No. 187-1320, Nalgene Conapany, Rochester, N.Y.). The syringes were placed in racks and lyophilized using the following lyophilization cycle in the lyophilizer (Model 15 SRC-X, Virtis Company, Gardiner, N.Y.).

|  | Set Point | Ramp Time | Soak Time | Vacuum |
| --- | --- | --- | --- | --- |
| Segment 1 | −40° C. | 1.0 hr | 5.0 hr | OFF |
| Segment 2 | −5° C. | 3.0 hr | 3.0 hr | ON |
| Segment 3 | +20° C. | 2.0 hr | 12.0 hr | ON |

Example 3

(HPLC Analysis of Lyophilized DSG-PEG)

The following experiment was performed to measure the activity of lyophilized DSG-PEG to determine if lyophilization had resulted in an unacceptable loss of activity of the DSG-PEG:

The contents of syringes prepared according to the procedure described in Example 2 were analyzed by HPLC for DSG-PEG content and compared to an aqueous control sample of DSG-PEG which had been solubilized and sterile-filtered. Lyophilized samples were analyzed for DSG-PEG content immediately after lyophilization and again after 2-week storage with a desiccant at room temperature. The aqueous control sample of DSG-PEG was analyzed approximately 2 hours after solubilization. HPLC analysis of DSG-PEG samples was performed using an isocratic elution. Conditions of HPLC analysis were as follows:

| | |
| --- | --- |
| Column: | Waters Ultrahydrogel 250 |
| Pore Size: | 250 Angstroms |
| Column Size: | 7.8 mm × 30 cm |
| Exclusion Limit: | $8 \times 10^4$ daltons |
| Injection Volume: | 20 μl |
| Mobile Phase: | 5 mM Sodium Acetate buffer, pH = 5.5 at 21° C. |
| Flow Rate: | 0.5 ml/min |
| Pressure: | 0.8 mPa |
| Detector: | Dual Detector System, Refractive Index & UV at 260 nm |

An external standard calibration curve was obtained using PEG solutions of various concentrations. The stock solution was prepared by dissolving 10.0 mg of difunctionally activated SG-PEG in 1.000 ml of deionized water. The solution was sequentially diluted to 5.00, 2.50, 1.25, 0.625, and 0.3125 mg/ml and analyzed by HPLC. Integrating the peak at a retention time of 16 minutes, the peak area was plotted against each concentration of DSG-PEG standard.

The aqueous control sample of DSG-PEG showed 76.3% retention of difunctionality, as compared to 74.1% for the sample tested immediately following lyophilization, and 73.9% (average of two samples) for samples tested after 2-week storage with desiccant at room temperature. Difunctionality is a measure of the potential ability of a substance to crosslink two or more molecules of collagen and/or other biocompatible polymer (i.e., "monofunctional" polymer molecules are not capable of performing crosslinking because they contain only one functional group and are therefore capable of reacting with only one molecule of biocompatible polymer.)

Example 4

(Stability of Previously Frozen SG-PEG Solutions)

The following experiment was performed to determine if solutions of difunctionally activated SG-PEG in water-for-injection would retain their activity when frozen for periods of time as long as 3 weeks in order to determine if DSG-PEG solutions could be pre-frozen, then lyophilized in large batches.

A solution having a concentration of 10 milligrams of DSG-PEG per milliliter of WFI (pH 4.5) was prepared. The DSG-PEG solution was aliquotted, 1 ml each, into Eppendorf tubes. A control sample was removed for HPLC analysis. The remainder of the samples were placed in a freezer at −20° C. Samples were removed from the freezer at various time intervals, allowed to thaw at room temperature for 10 minutes, then analyzed for DSG-PEG content by HPLC according to the procedure detailed in Example 3. Results of HPLC analysis are presented in Table 3.

TABLE 3

HPLC Analysis of Previously Frozen DSG-PEG in WFI

| Time | % DSG-PEG |
|---|---|
| 0 (Control) | 86.3 |
| 2 hours | 84.6 |
| 1 day | 82.7 |
| 2 days | 82.4 |
| 3 days | 80.7 |
| 6 days | 83.5 |
| 8 days | 82.2 |
| 22 days | 78.6 |

Results show that DSG-PEG in WFI retains at least 90% of its original activity upon freezing for up to 22 days at −20 C.

The four cylindrical gels of PEG-crosslinked collagen prepared in Example 5 were pushed out of their respective syringes, then sliced into disks having a thickness of 5 mm each. Gel strength of each of the PEG-collagen disks was measured by compressing the disks to failure using the Insiron Model 4202 Universal Testing Instrument with 100 Newton Static Load Cell. Gel strength for each of the four formulations is presented in Table 4.

TABLE 4

Gel Strength Measurements for PEG-Collagen Formulations

| Crosslinking Agent Composition: | DSG-PEG/ Glucose/PEG | Gel Strength (in Newtons) | | DSG-PEG/ NaCl/PEG |
|---|---|---|---|---|
| | | DSG-PEG/Glucose | DSG-PEG/NaCl | |
| Sample 1 | 39.4 | 28.3 | 34.6 | 32.7 |
| Sample 2 | 24.9 | 29.1 | 38.0 | 30.1 |
| Sample 3 | 27.0 | 25.0 | 39.4 | 37.9 |
| Sample 4 | 35.7 | 27.1 | n/a | 39.7 |
| Average | 31.8 | 27.4 | 37.3 | 35.1 |

Example 5

(Preparation of a Dry Crosslinking Agent: Pelletization of DSG-PEG)

Difunctionally activated SG-PEG (DSG-PEG, 3800 MW) was pelleted with glucose, unactivated polyethylene glycol (PEG), and/or sodium chloride. The dry reagents were mixed using a mortar and pestle, then loaded into a compression mold to form pellets. The following four formulations were prepared:

| | |
|---|---|
| Formulation 1: | 7.5 mg DSG-PEG, 30.0 mg glucose, 7.5 mg PEG (DSG-PEG/Glucose/PEG) |
| Formulation 2: | 7.5 mg DSG-PEG, 37.5 mg glucose (DSG-PEG/Glucose) |
| Formulation 3: | 7.5 mg DSG-PEG, 75.0 mg NaCl (DSG-PEG/NaCl) |
| Formulation 4: | 7.5 mg DSG-PEG, 30.0 mg NaCl, 7.5 mg PEG (DSG-PEG/NaCl/PEG) |

Each of the four pellets was placed in the barrel of a 3.0-cc syringe and mixed with 1.5 cc of Zyderm®Collagen (35 mg/ml collagen concentration, available from Collagen Corporation, Palo Alto, Calif.) in a 3.0-cc syringe. The pellets quickly solubilized when contacted with the collagen. The collagen and pellets were mixed for 2 minutes using syringe-to-syringe mixing, as previously described. All of the material for each formulation was transferred into one syringe, then allowed to crosslink within the syringe for 3 hours. Each of the four formulations had a molar ratio of approximately 12 moles of DSG-PEG per mole of collagen.

Example 6

(Gel Strength Testing of Collagen Crosslinked with Pelletized DSG-PEG)

All four gels showed good gel strength, particularly the gels containing sodium chloride, which may be due to partial disassembly of the collagen fibers by sodium chloride resulting in more sites being available on the collagen for crosslinking with difunctionally activated SG-PEG. As non-crosslinked collagen has no gel strength (i.e., gel strength=0 Newtons), the data presented in Table 1 indicate that crosslinking has occurred between collagen and DSG-PEG using dry DSG-PEG, with or without glucose or sodium chloride.

Factors such as pH, which may vary in vivo depending on the site of injection, may affect the rate of the crosslink reaction between the collagen and the crosslinking agent, as well as the gel strength of the resulting crosslinked collagen implant.

Example 7

(Method of Preparing and Administering Crosslinked Collagen Compositions for Soft Tissue Augmentation)

A physician opens a kit containing the following components: one 3-cc syringe containing 1 ml of Zyderm® I Collagen; one 3-cc syringe containing 10 mg of sterile, dry, difunctionally activated SG-PEG (DSG-PEG, MW 3800); one empty 1-cc syringe; one three-way stopcock; and several 30-gauge needles. The physician connects the syringe containing the Zyderm Collagen with the syringe containing the dry DSG-PEG by means of the three-way stopcock. She then mixes the collagen and DSG-PEG back and forth between the syringes, employing 40 passes of material between the syringes. She then transfers all of the material into one of the 3-cc syringes, detaches the empty 3-cc syringe from the stopcock, attaches the empty 1-cc syringe to the 3-cc syringe containing the collagen and DSG-PEG by means of the stopcock, then transfers the entire contents of the 3-cc syringe into the formerly empty 1-cc syringe. She then attaches one of the 30-gauge needles to the full 1-cc syringe.

After attaching the needle to the syringe, the physician injects the collagen and DSG-PEG (which have since initiated crosslinking) subcutaneously, using multiple serial punctures, to soft tissue sites in need of augmentation, such as acne scars and wrinkles. Treatment of the patient is completed within 20 minutes of mixing the collagen and the DSG-PEG.

What is claimed is:

1. A method of preparing a formed implant comprising a crosslinked biomaterial composition comprising the steps of:
    providing a device for extruding a biocompatible polymer and a device for extruding a sterile, dry crosslinking agent;
    mixing the biocompatible polymer and the crosslinking agent to initiate crosslinking between the biocompatible polymer and the crosslinking agent;
    extruding the biocompatible polymer and the crosslinking agent into a mold having a desired size and shape; and
    allowing the biocompatible polymer and the crosslinking agent to crosslink within the mold to produce a formed implant having a desired size and shape.

2. The method of claim 1, wherein the biocompatible polymer is selected from the group consisting of collagen, a collagen derivative, a glycosaminoglycan, a glycosaminoglycan derivative, and mixtures thereof.

3. The method of claim 2, wherein the collagen is atelopeptide fibrillar collagen.

4. The method of claim 2, wherein the glycosaminoglycan is selected from the group consisting of: hyaluronic acid, chondroitin sulfate A, chondroitin sulfate C, dermatan sulfate, keratan sulfate, keratosulfate, chitin, chitosan, heparin, and mixtures thereof.

5. The method of claim 1, wherein the crosslinking agent is a synthetic hydrophilic polymer containing a functional group capable of forming a covalent bond with a primary amino group on a biocompatible polymer molecule.

6. The method of claim 5, wherein synthetic hydrophilic polymer is a polyethylene glycol that has been chemically derivatized to contain a functional group capable of forming a covalent bond with a primary amino group on a biocompatible polymer molecule.

7. The method of claim 6, wherein the polyethylene glycol has been chemically derivatized to contain two functional groups capable of forming covalent bonds with primary amino groups on biocompatible polymer molecules.

8. A method of providing a coating comprising a crosslinked biomaterial composition on a surface of a synthetic implant comprising the steps of:
    providing a device for extruding a biocompatible polymer and a device for extruding a sterile, dry crosslinking agent;
    mixing the biocompatible polymer and the crosslinking agent to initiate crosslinking between the biocompatible polymer and the crosslinking agent;
    extruding the biocompatible polymer and the crosslinking agent onto a surface of a synthetic implant; and
    allowing the biocompatible polymer and the crosslinking agent to crosslink on the surface of the synthetic implant to provide a crosslinked biomaterial coating on the surface of the implant.

9. The method of claim 8, wherein the biocompatible polymer is selected from the group consisting of collagen, a collagen derivative, a glycosaminoglycan, a glycosaminoglycan derivative, and mixtures thereof.

10. The method of claim 9, wherein the collagen is atelopeptide fibrillar collagen.

11. The method of claim 9, wherein the glycosaminoglycan is selected from the group consisting of: hyaluronic acid, chondroitin sulfate A, chondroitin sulfate C, dermatan sulfate, keratan sulfate, keratosulfate, chitin, chitosan, heparin, and mixtures thereof.

12. The method of claim 8, wherein the crosslinking agent is a synthetic hydrophilic polymer containing a functional group capable of forming a covalent bond with a primary amino group on a biocompatible polymer molecule.

13. The method of claim 12, wherein the synthetic hydrophilic polymer is a polyethylene glycol that has been chemically derivatized to contain a functional group capable of forming a covalent bond with a primary amino group on a biocompatible polymer molecule.

14. The method of claim 13, wherein the polyethylene glycol has been chemically derivatized to contain two functional groups capable of forming covalent bonds with primary amino groups on biocompatible polymer molecules.

* * * * *